United States Patent
Bohn et al.

(10) Patent No.: US 7,993,058 B2
(45) Date of Patent: Aug. 9, 2011

(54) LAMELLA COLLIMATOR AND BEAM THERAPY APPLIANCE

(75) Inventors: Robert Bohn, Schriesheim (DE); John Juschka, Eberach (DE); Petra Juschka-Lenz, legal representative, Eberach (DE); Stefan Leidenberger, Effeltrich (DE); Rene Schramm, Wilhelmsfeld (DE)

(73) Assignee: Siemens Aktiengesellschaft, Munich (DE)

( * ) Notice: Subject to any disclaimer, the term of this patent is extended or adjusted under 35 U.S.C. 154(b) by 73 days.

(21) Appl. No.: 12/438,301

(22) PCT Filed: Jul. 31, 2007

(86) PCT No.: PCT/EP2007/057908
§ 371 (c)(1),
(2), (4) Date: Aug. 18, 2009

(87) PCT Pub. No.: WO2008/022879
PCT Pub. Date: Feb. 28, 2008

(65) Prior Publication Data
US 2010/0008472 A1    Jan. 14, 2010

(30) Foreign Application Priority Data
Aug. 24, 2006  (DE) .......................... 10 2006 039 793

(51) Int. Cl.
G21K 1/04    (2006.01)
A61B 6/08    (2006.01)
A61N 5/10    (2006.01)

(52) U.S. Cl. ........... 378/205; 378/65; 378/152; 378/153

(58) Field of Classification Search .................. 378/152, 378/153, 65, 205
See application file for complete search history.

(56) References Cited

U.S. PATENT DOCUMENTS

| 4,868,843 | A  * | 9/1989  | Nunan ........................... 378/152 |
| 5,555,283 | A  * | 9/1996  | Shiu et al. ...................... 378/151 |
| 6,696,694 | B2 * | 2/2004  | Pastyr et al. ................. 250/505.1 |
| 6,711,237 | B1   | 3/2004  | Schlegel et al. |
| 6,730,924 | B1 * | 5/2004  | Pastyr et al. ................. 250/505.1 |
| 7,564,951 | B2 * | 7/2009  | Hasegawa et al. ............ 378/152 |
| 7,629,599 | B2 * | 12/2009 | Hashimoto ................. 250/505.1 |
| 2008/0292058 | A1 | 11/2008 | Nagata |

FOREIGN PATENT DOCUMENTS

| DE | 196 39 861 A1   | 4/1997 |
| DE | 199 04 972 A1   | 8/2000 |
| DE | 100 45 260 C1   | 1/2002 |
| WO | WO/0046813      | 8/2000 |
| WO | WO 2005/068019 A1 | 7/2005 |

OTHER PUBLICATIONS

German Office Action dated Mar. 5, 2007 with English translation.
PCT Written Opinion dated Nov. 2007 with English translation.

* cited by examiner

*Primary Examiner* — Edward J Glick
*Assistant Examiner* — Thomas R Artman
(74) *Attorney, Agent, or Firm* — Lempia Summerfield Katz LLC

(57) ABSTRACT

A lamella collimator, in particular for a beam therapy appliance, is provided. The lamella collimator has a plurality of lamellae, which can be moved by a motor or motors in a movement direction in order to preset a countour of a beam path on an X-ray beam. Each lamella has a position measurement apparatus with a movable measurement element, which is attached directly to the respective lamella.

12 Claims, 5 Drawing Sheets

LAMELLA COLLIMATOR AND BEAM THERAPY APPLIANCE

The present patent document claims the benefit of the filing date of DE 10 2006 039 793.2, filed Aug. 24, 2006, which is hereby incorporated by reference. The present patent document also claims the benefit of the filing date of PCT/EP2007/057908 filed Jul. 31, 2007, which is also incorporated by reference.

BACKGROUND

The present embodiments relate to a lamella collimator. In particular, the present embodiments relate to a beam therapy appliance, and to a beam therapy appliance with a lamella collimator.

A lamella collimator is used in radiation therapy for the treatment of tumors. DE 196 39 816 A1 and WO 00/46813 describe lamella collimators. During radiation therapy, a tumor is irradiated with high-energy beams, generally with high-energy X-ray radiation from a linear accelerator. The lamella collimator may be placed in the beam path of the X-ray beam. The lamella collimator includes a plurality of lamellae that can be displaced against each other by a motor to define an aperture with a contour corresponding to the contour of the tumor. Only the tumor is irradiated with the X-rays; not the adjacent healthy body tissue. Two sets of lamellae may be arranged in relation to each other in such a way that their end faces can be moved toward and away from each other. As a result, virtually any tumor contour may be modeled.

Each of these lamellae can be individually displaced by an electric motor. During the positioning of a lamella, there can be slight deviations between a desired value and the actual set position of the lamella. Each lamella includes a position measurement apparatus with which the actual position set can be determined.

Particularly narrow lamellae are used to model very fine contours. DE 196 39 861 A1 describes a lamella collimator with narrow lamellae. In addition, the lamellae of the lamella collimator are often arranged in a semicircular shape in the beam direction and slightly inclined toward each other. This is a reliable way of avoiding narrow gaps between the individual lamellae, which greatly reduce the shielding effect of the lamella collimator in this region and would result in the irradiation of healthy body tissue.

With the lamella collimator described in DE 196 39 861 A1, the individual lamellae are provided on their upper edges on the side facing way from the beam side with oblong connecting cords, the other end of which engage the cords of a position measurement apparatus, which is not shown, for example by ball connectors. For reasons of space, as seen from the direction of travel of the lamellae, the connecting cords spread out in a fan shape, like that in a mechanical typewriter.

The mechanical connection of the individual position measurement apparatuses to individual lamellae is very complicated.

SUMMARY AND DESCRIPTION

The present embodiment may obviate one or more of the limitations or drawbacks inherent in the related art. For example, in one embodiment, a lamella collimator includes a simplified and easy-to-maintain position measurement apparatus. A beam therapy appliance may include the lamella collimator.

In one embodiment, for each lamella, the lamella collimator may include a position measurement apparatus with a movable measuring element that is attached directly to the associated lamella. A structural connection between a lamella and the associated position measurement apparatus may not be needed using an intermediate element, such as, for example, a strip-like connecting cord. According to the prior art, these connecting elements have an oblong design and spread out in a fan shape, there is always also the risk of the individual connecting elements interlocking. This risk of interlocking no longer exists when the position measurement apparatus is directly connected to a lamella. The operational reliability of the lamella collimator is also increased. There is no need for the complex mechanical alignment of the individual connecting cords during production.

In one embodiment, the attachment of the measurement element to the lamella is a joint. With lamellae that are obliquely inclined toward each other, the connection of the position measurement apparatus is simplified. The use of a joint avoids or at least greatly reduces mechanical stresses. The joint is, for example, a ball-and-socket joint or as a hinge joint.

In one embodiment, the measurement element and the lamella are attached to each other by a connection including a bolt and a bolt holder. A bolt connection is simple to make. A bolt can be made in such a way that it is constructed no wider than the lamella. Therefore, the measurement element can be attached directly behind the lamella in a particularly space-saving way. If the bolt holder is also embodied rotatably in the longitudinal direction of the bolt, the measurement element can be moved against the lamella in the manner of a hinge.

The bolt includes a detent groove for latching and fixing in the bolt holder. Therefore, the connection between the bolt and the bolt holder is secured in such a way that the bolt is unable to slip out of the bolt holder. This reliably prevents any failure of the position measurement apparatus.

In one embodiment, the position measurement apparatus includes a measuring plate as a measurement element and a plate holder for holding this measuring plate. An essentially plate-shaped measurement element is particularly simple to make. If the corresponding plate holder is provided with side walls aligned parallel to each other, the measuring plate can slide back and forth in this plate holder with virtually no friction resistance when the lamella is displaced in the movement direction. As a result, the displacement of the lamella is not impeded. The measuring plate lies flat on the wall of the plate holder and achieves good contact between the measurement element and the plate holder.

In one embodiment, in the longitudinal direction and parallel to the movement direction of the lamella collimator, the measuring plate comprises at least one guide rail as a guide element to guide it along a contour of the corresponding plate holder. As a result, there is particularly reliable guidance of the measuring plate in the plate holder.

At least two guide rails are arranged opposite to each other on the measuring plate in the transverse direction and perpendicularly to the beam direction and to the movement direction. Since both these guide rails are guided by a contour of the corresponding plate holder, fail-safe guidance of the measuring plate is achieved.

In one embodiment, the position measurement apparatus is a potentiometer. A potentiometer may be used to measure a resistance proportional to the position of the lamella. The resistance measurement can be implemented in a cost-effective way.

In one embodiment, the measuring plate includes at least one contact element and the plate holder sliding contact corresponding to the contact element. With a flat embodiment of both the contact element and the corresponding sliding contact, the position measurement apparatus, embodied as a potentiometer, can achieve a reliable and precise measurement.

Each contact element is attached to the measuring plate by at least one fixing element. For example, the at least one fixing element is a stud onto which the contact element provided with a stud holder can be simply plugged. The contact element can be assembled or replaced easily so that the ease-of-maintenance of the position measurement apparatus of the lamella collimator is greatly increased.

In one embodiment, the plate holder and the measuring plate guided and held are essentially arranged in the beam direction above the upper transverse side or below the lower transverse side of the lamella. As a result, the displacement of the individual lamellae in the movement direction is not impeded and, a plurality of plate holders can be combined in the form of a module so that the assembly of this module inside the lamella collimator is greatly simplified and that it may be replaced quickly in the event of an error. The production of plate holders arranged next to each other in module form reduces the production costs enormously.

In one embodiment, the measuring plate is made of plastic. A measuring plate made of plastic has a low moving mass. As a result, the risk of interlocking and blocking of the measuring plate and the lamella during displacement is greatly reduced. The production of the measuring plate from a plastic can be achieved in a particularly cost-effective manner.

In one embodiment, the position measurement apparatuses of adjacent lamellae are arranged in the beam direction in alternation above the upper transverse sides and below the lower transverse sides. In the case of lamellae with a particularly narrow design, the associated measuring plates with their measuring holders are designed wider than the individual lamellae. The alternating arrangement enables, viewed over the width, twice as many plate holders to be accommodated, which are then arranged respectively above the upper and below the lower transverse sides of the lamellae.

The object is also achieved by a beam therapy appliance with a lamella collimator. The advantages described for the preferred embodiments with respect to the lamella collimator may also be transferred to a beam therapy appliance with a lamella collimator of this kind.

DETAILED DESCRIPTION

Figure 1:
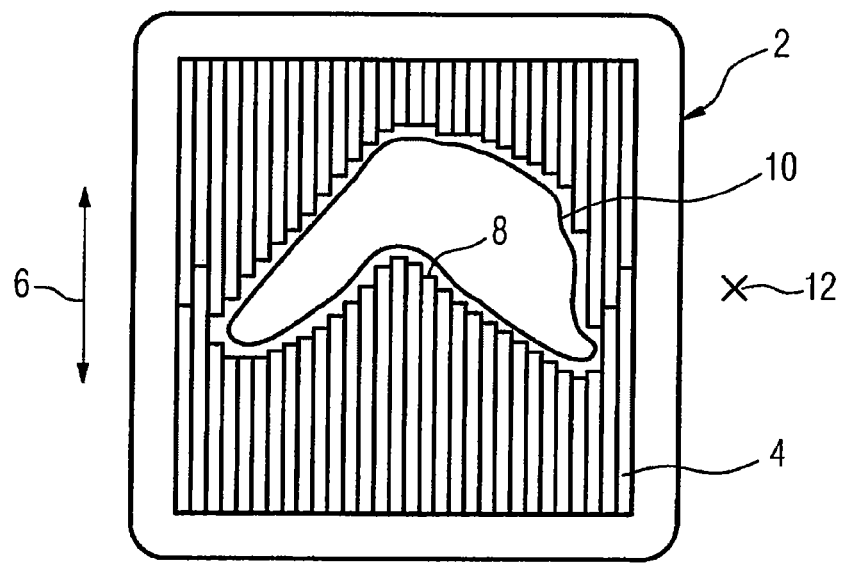
FIG. 1 illustrates a schematic top view of a lamella collimator.

FIG. 1 shows is a schematic top view of a lamella collimator 2 including a plurality of plate-type lamellae 4 arranged essentially parallel to each other. These lamellae 4 can be displaced in the movement direction 6 by a motor. For the displacement, in each case, the front end faces 8 of two lamellae 4 lying opposite to each other are moved toward or away from each other. As a result, it is possible to set virtually any contour 10 for the irradiation of a tumor with an X-ray beam passing through the lamella collimator 2 in the beam direction 12. In FIG. 1, viewed from the image plane, this X-ray beam 12 passes from top to bottom through the irradiation contour 10 through the lamella collimator 2.

Figure 2:
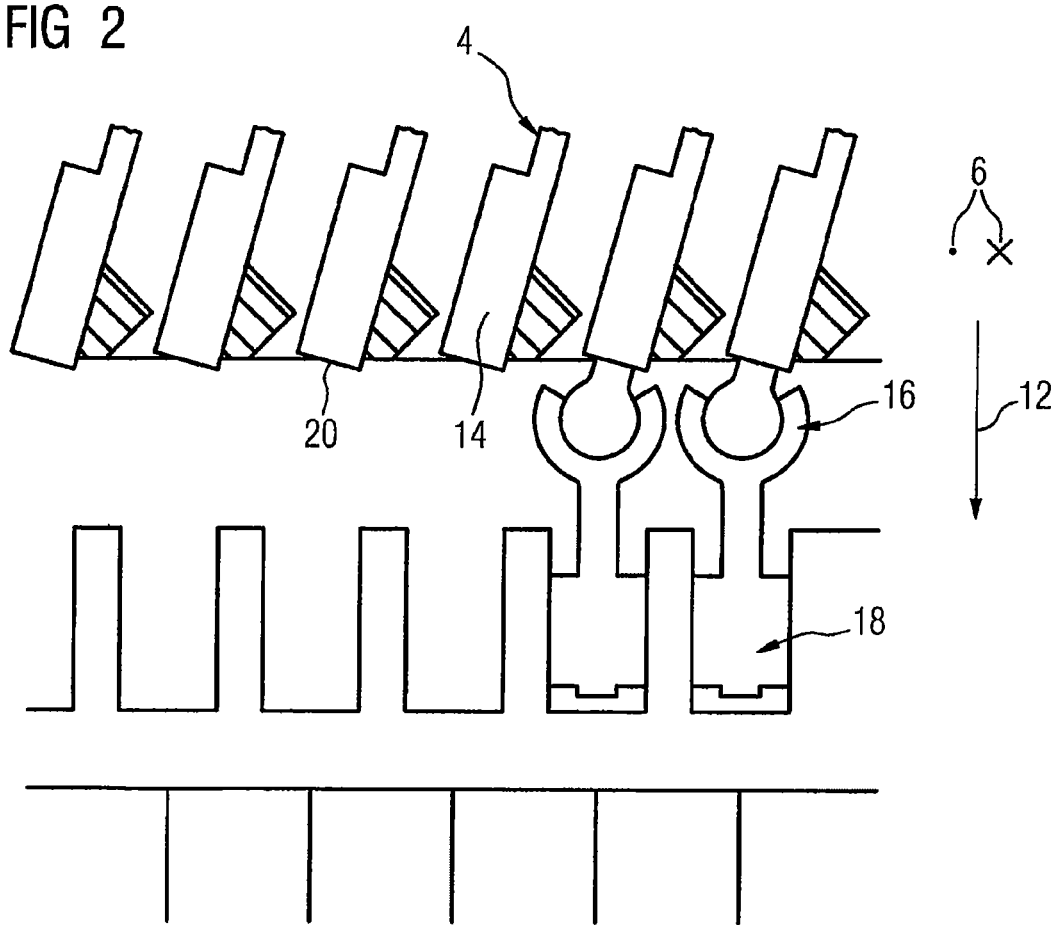
FIG. 2 illustrates another schematic view of a position measurement apparatus view from the rear end face of the lamella collimator.

FIG. 2 illustrates a plurality of lamellae in a slightly angled alignment viewed from their rear end faces 14. Viewed over the entire width, all the lamellae 4 are aligned in a slightly semi-circular shape with respect to each other. This avoids gaps, which would result in the passage of X-ray radiation outside the contour 10. FIG. 2 shows the beam direction 12 running from top to bottom. However, the X-ray beam also passes outside the image plane in the region of the front end faces 8 of the lamellae 4.

At each rear end face 14 of a lamella 4, a position measurement apparatus 18 is attached directly by a joint 16. For purposes of clarity, the drawing only shows only two position measurement apparatuses 18. These position measurement apparatuses 18 are arranged on the lower transverse sides 20 of the lamellae 4, viewed from the beam direction.

Figure 3:
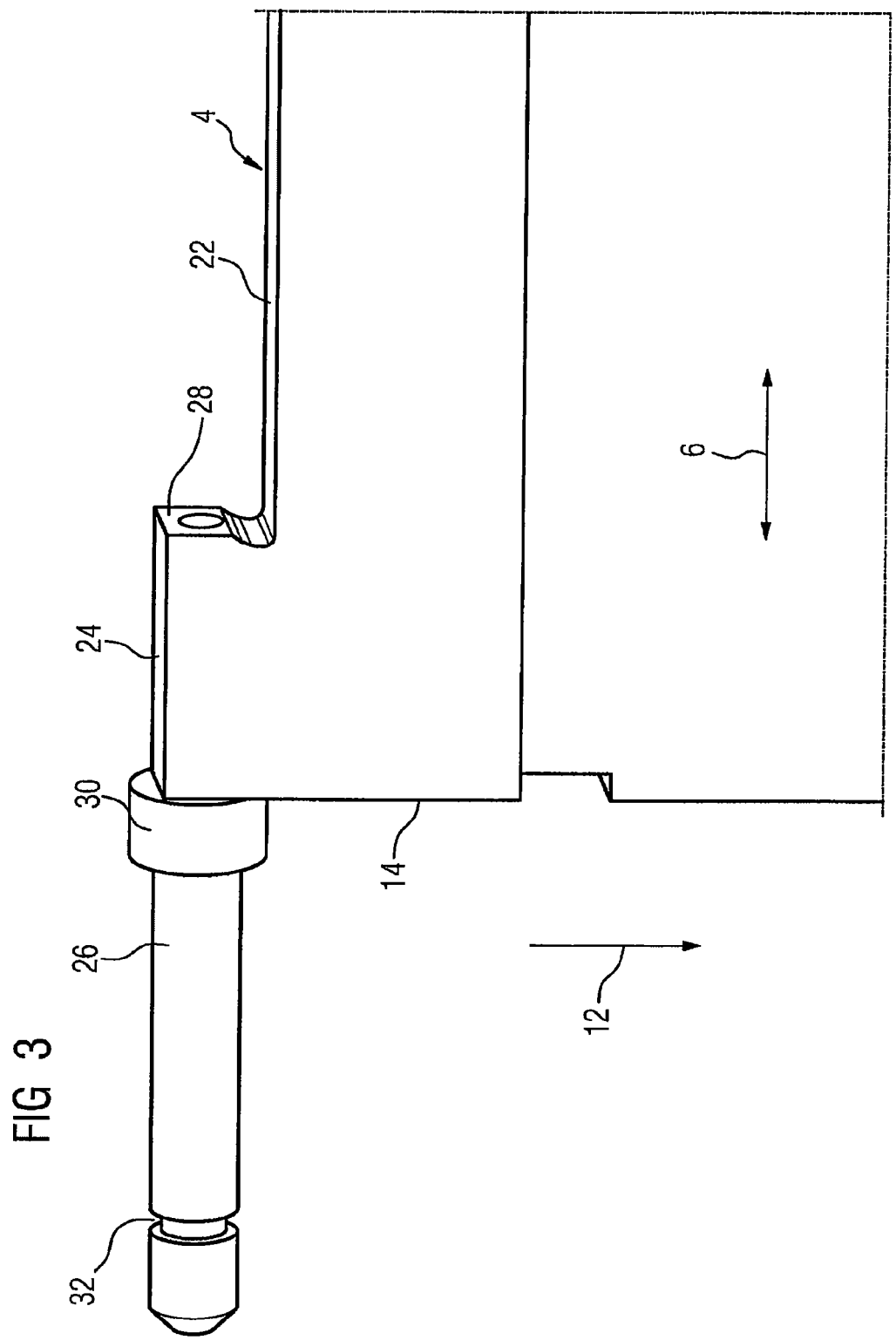
FIG. 3 illustrates the upper end of the side of a lamella facing away from the beam with a bolt.
Figure 4:
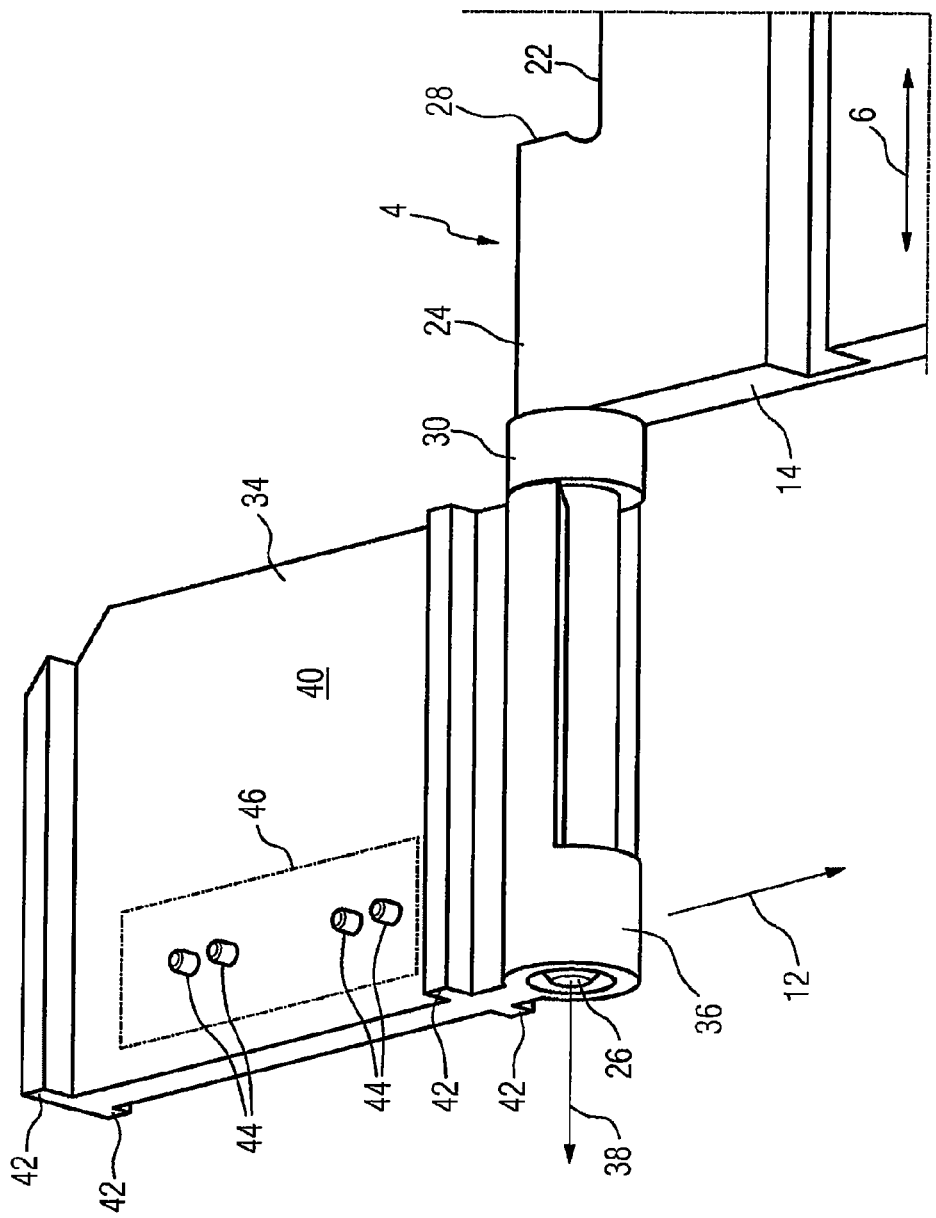
FIG. 4 illustrates another view of the end the lamella facing away from the beam with a measuring plate pushed onto the bolt measuring plate.
Figure 5:
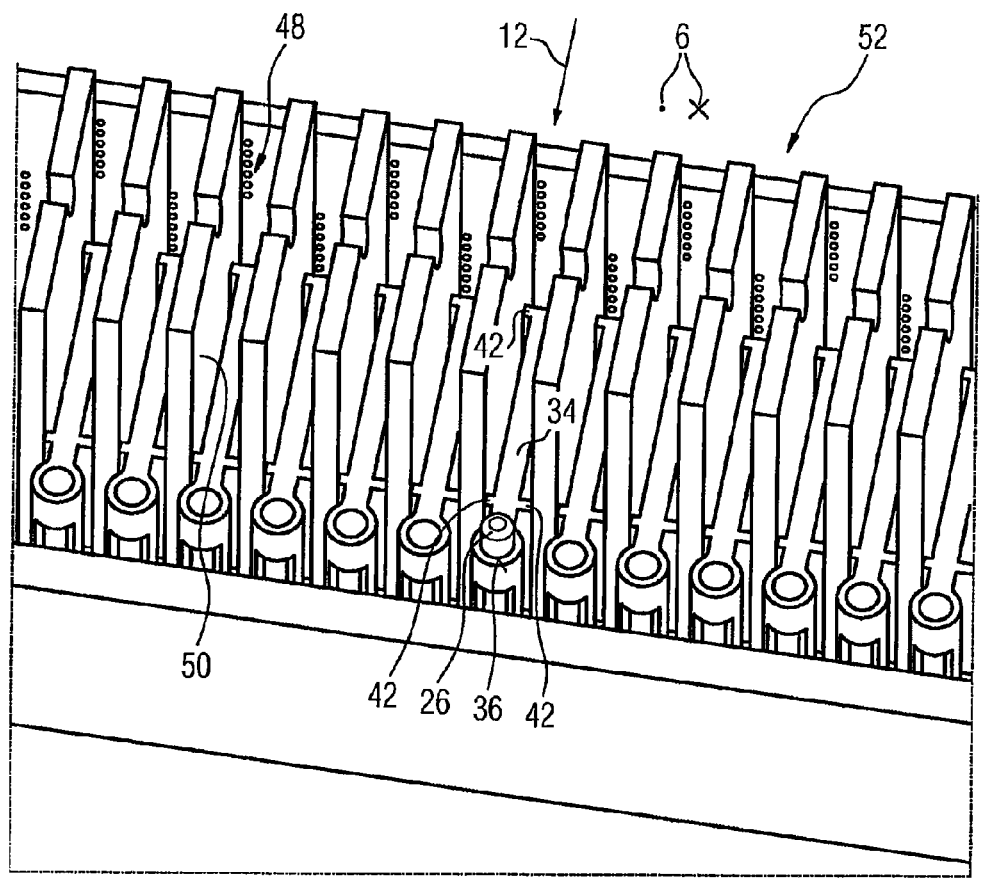
FIG. 5 illustrates a plurality of measuring plates in plate holders arranged next to each other and FIG. 6 illustrates a schematic view of a beam therapy appliance with a lamella collimator.

FIGS. 3 to 5 show the embodiment of a position measurement apparatus 18 in more detail.

FIG. 3 shows a lamella 4 in the region of its rear end face 14 and the upper transverse side 22. A bolt holder 24 is attached counter to the beam direction 12 above the upper transverse side 22. One end of a bolt 26 is held and fixed in the bolt holder 24 by a fixing bore. During a displacement of the lamella 4 in the movement direction 6 toward the beam region, the end face 28 of the bolt holder 24 facing the X-ray beam in the movement direction 6 serves as an end stop so that the lamella 4 cannot be further moved.

The cylindrical bolt 26 extends from the rear end face 14 of the lamella 4 parallel to the movement direction 6 from the rear end face. It has an assembly stop 30 and a detent groove 32 for fixing a measuring plate shown in FIG. 4.

FIG. 4 shows a lamella 4 in the region of its rear end face 14 and its upper transverse side 22. A measuring plate 34, with a bolt holder 36 embodied as a hollow cylinder, is pushed onto the bolt 26. The measuring plate 34 is pushed on as far as the assembly stop 30 of the bolt 26 so that the detent groove 32 of the bolt latches in a contour of the bolt holder 3. The measuring plate 34 is attached directly to the lamella 4 by the bolt 26. In the movement direction 6 of the lamella 4, no movement of the measuring plate 34 relative to the lamella 4 is possible. However, the measuring plate 34 can be swiveled about the central longitudinal axis 38 of the bolt 26 in the manner of a hinge.

The measuring plate 34 includes a plate body 40 counter to the beam direction above the bolt holder 36. Close to the bolt holder 36, the plate body 40 includes two opposing guide rails 42 extending in its transverse direction parallel to the upper transverse side 22 of the lamella 4 and perpendicular to the movement direction 6. The plate body 40 includes, at its end lying opposite to the bolt holder 36, a further two opposing guide rails 42. Attached to both sides of the surface of the plate body 40 are in each case four lug-like fixing elements 44 to each of which a contact element can be latched, the contour 46 of which is indicated in FIG. 4.

Each measuring plate 34 is pushed into a corresponding plate holder 48 as shown in FIG. 5.

FIG. 5 shows a plurality of plate holders 48 arranged next to each other, into each of which a measuring plate 34 is inserted and held. The side walls 50 of the plate holders 48 are aligned parallel to each other. Inserted in the side walls 50 of the plate holders 48 in FIG. 5 are guide contours, so that each measuring plate 36 is reliably held and guided in the plate holder 48 by its two pairs of guide rails 42.

The position measurement apparatus 18 functions according to the principle of a potentiometer. Each contact element 46 of a measuring plate 34 comes into contact with a sliding contact arranged on one of the two side walls 50 of a plate holder 48. The combination of the contact element 46 and the sliding contact forms a potentiometer circuit. A displacement of the measuring plate 34 in the corresponding plate holder 48 causes the resistance of the potentiometer circuit to change. The change in the resistance is proportional to the local position of the lamella 4 in the movement direction 6. A potentiometer circuit of this kind can be established in a particularly simple and cost-effective way.

FIG. 5 is summary of a plurality of plate holders 48 in a measuring module 52.

The measuring plate 34 with its guide rails 42 is wider than a lamella 4. In addition, the width of the side walls 50 of the plate holder 48 takes up space. Only every second lamella 4 has a position measurement apparatus 18 to be positioned above its upper transverse side 22. The intermediate lamellae 4 include a position measurement apparatus 18 arranged similarly to the depiction in FIG. 2 on its lower transverse side 20.

A measuring module 52 with plate holders aligned parallel to each other is arranged above the upper transverse sides 22 of the lamellae. A measuring module 52 is arranged below the lower transverse sides 20 of the lamellae.

This enables the direct connection of the position measurement apparatuses 18 to the lamellae 4 even in the case of lamellae 4 with a narrow design. In the event of a fault, a measuring module 52, including a plurality of plate holders 48, can easily be exchanged as a whole. No complex adjustment work, such as that in the case of the connection of position measurement apparatuses via connecting cords to the lamellae, is required. Despite the inclination of the lamellae 4, due to the position measurement apparatus 18 attached by a joint 16 to each lamella 4, the parallel alignment of the side walls 50 of the plate holders 48 is possible, since the joints 16 counteract the occurrence of mechanical stresses. This in turn reduces the production costs.

Figure 6:
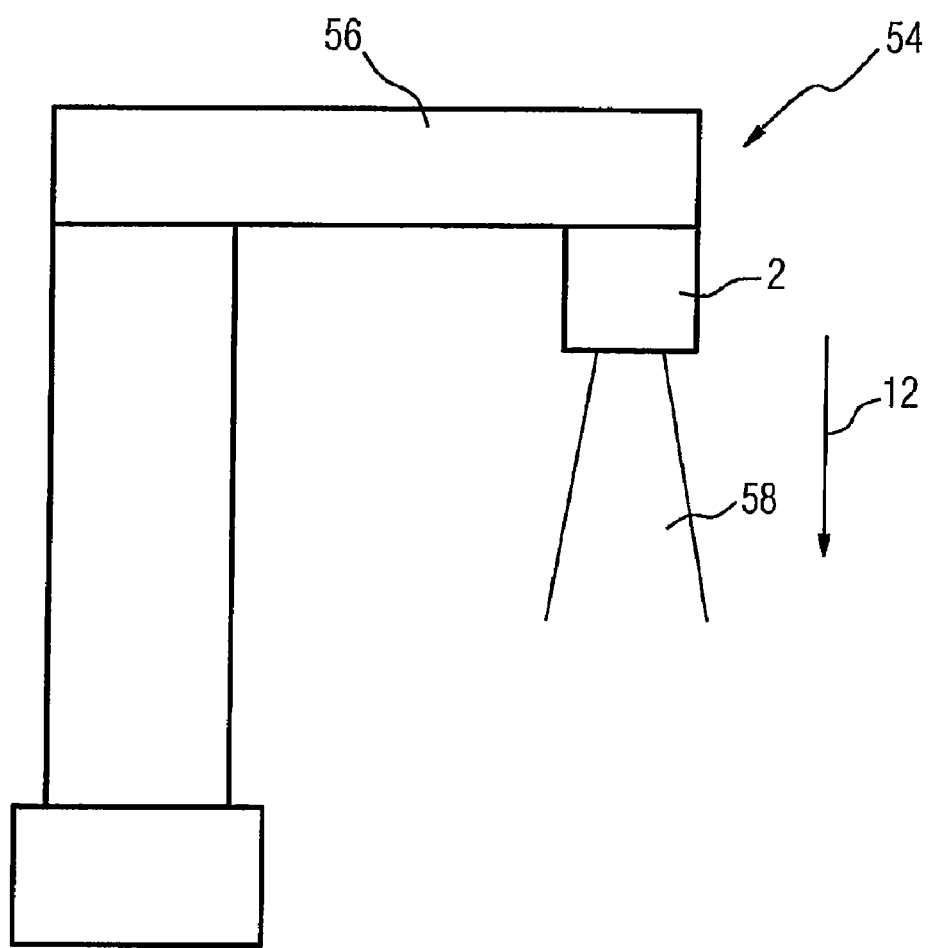

FIG. 6 shows a schematic side view of a beam therapy appliance 54 including a holding device 56 and a lamella collimator 2 arranged in a housing. By a focusing mimic, the X-ray beam 58 passes through the lamella collimator 2 in the beam direction 12. The lamella collimator 2 defines a contour 10 for the irradiation of a tumor by its individual movable lamella 4.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A lamella collimator for a beam therapy appliance, the collimator comprising:
    a plurality of lamellae that is operable to be moved by a motor in a movement direction in order to preset a contour of a beam path of an X-ray beam, with one position measurement apparatus per lamella including a movable measurement element,
    wherein the respective movable measurement element is attached directly to the respective lamella,
    wherein the movable measurement element is pivotably attached to the lamella, and
    wherein the movable measurement element and the lamella are attached to each other via a connection including a bolt and a bolt holder.

2. The lamella collimator as claimed in claim 1, wherein the bolt and the bolt holder are latched to each other to fix the bolt to the bolt holder.

3. The lamella collimator as claimed in claim 1, wherein the one position measurement apparatus comprises a measuring plate and a plate holder, the measuring plate being the movable measurement element.

4. The lamella collimator as claimed in claim 3, wherein the measuring plate includes at least one guide element in a longitudinal direction to guide the measuring plate on the corresponding plate holder.

5. The lamella collimator as claimed in claim 4, wherein at least two guide elements are arranged opposite to each other on the measuring plate.

6. The lamella collimator as claimed in claim 1, wherein the one position measurement apparatus comprises a potentiometer.

7. The lamella collimator as claimed in claim 3, wherein the measuring plate comprises at least one contact element.

8. The lamella collimator as claimed in claim 7, wherein the at least one contact element is attached to the measuring plate by at least one fixing element.

9. The lamella collimator as claimed in claim 3, wherein the plate holder and the measuring plate guided and held by the plate holder are, with reference to a beam direction, arranged above an upper transverse side or arranged below a lower transverse side of the lamella.

10. The lamella collimator as claimed in claim 3, wherein the measuring plate is made of a plastic.

11. The lamella collimator as claimed in claim 1, wherein the position measurement apparatuses of adjacent lamellae are arranged in alternation on opposing sides of the lamellae.

12. A beam therapy appliance comprising:
    a lamella collimator comprising:
        a plurality of lamellae that is operable to be moved by a motor in a movement direction in order to preset a contour of a beam path of an X-ray beam, with one position measurement apparatus per lamella including a movable measurement element,
    wherein the respective movable measurement element is attached directly to the respective lamella,
    wherein the movable measurement element is pivotably attached to the lamella, and
    wherein the movable measurement element and the lamella are attached to each other via a connection including a bolt and a bolt holder.

* * * * *